United States Patent [19]

McDonnell et al.

[11] Patent Number: 5,279,611
[45] Date of Patent: Jan. 18, 1994

[54] LASER SHAPING OF OCULAR SURFACES USING ABLATION MASK FORMED IN SITU

[76] Inventors: Peter J. McDonnell, 3841 Keswick Rd., La Canada-Flintridge, Calif. 91011; Stephen L. Trokel, 165 E. 66th St., New York, N.Y. 10021

[21] Appl. No.: 850,726

[22] Filed: Mar. 13, 1992

[51] Int. Cl.$^5$ ............................................. A61N 5/06
[52] U.S. Cl. ........................................ 606/4; 128/898; 606/5
[58] Field of Search .................. 606/4, 5, 6; 128/898

[56] References Cited

U.S. PATENT DOCUMENTS

| | | | |
|---|---|---|---|
| 4,856,513 | 8/1989 | Muller | 606/5 |
| 4,969,912 | 11/1990 | Kelman et al. | 128/DIG. 8 |
| 4,994,058 | 2/1991 | Raven et al. | 128/897 |
| 5,071,417 | 12/1991 | Sinofsky | 606/12 |
| 5,133,708 | 7/1992 | Smith | 128/898 |

Primary Examiner—Stephen C. Pellegrino
Assistant Examiner—Sonya Harris
Attorney, Agent, or Firm—Robbins, Berliner & Carson

[57] ABSTRACT

A method for modification of the corneal surface, in which a gel is applied to the cornea and molded in situ to create an ablation mask. This ablation mask has a posterior surface substantially identical to that of the surface to be treated. A shaping means (such as a contact lens) having a posterior curvature corresponding to the desired final profile of the cornea is superimposed on the gel prior to the setting of the gel; the anterior curvature of the ablation mask is equal to that of the posterior curvature of the shaping means. The gel has essentially the identical ablation properties of the cornea, which is generally not the case when other non-biological materials (such as plastics materials) are used. A preferred gel for use in forming the ablation mask is collagen gel.

10 Claims, No Drawings

LASER SHAPING OF OCULAR SURFACES USING ABLATION MASK FORMED IN SITU

BACKGROUND OF THE INVENTION

The present invention relates to methods for the shaping of surfaces using lasers. In particular, the present invention relates to methods for the shaping of the cornea of the eye.

Many surgical procedures have been explored for reshaping the cornea. For example, to correct naturally occurring and postoperative astigmatism, procedures such as relaxing incisions (radial, transverse, arcuate), trapezoidal astigmatic keratectomy (Ruiz procedure), and wedge resection have been described. The number and the variety of techniques reflect the inability of any particular approach to provide adequate results in all patients (such as predictably eliminate corneal cylindrical error, in the case of astigmatism).

In a procedure known as radial keratotomy, radial incisions are made in the eye to remedy refractive errors such as myopia. The curvature of the eye is flattened when the incisions heal, thereby increasing the ocular focal distance.

The capacity of 193 nm argon-fluoride excimer laser to remove a precise amount of corneal tissue with submicron accuracy has let to clinical investigation of the excimer laser's ability to ablate corneal tissue so as to alter the curvature of the cornea for correction of refractive errors. This procedure is called photorefractive keratotomy (PRK).

The excimer laser can be utilized also to remove corneal opacities and other superficial corneal diseases in a procedure termed phototherapeutic keratotomy (PTK). PTK appears to be a useful and safe technique for treating corneal scarring from a variety of causes. However, approximately 50% of the patients experienced undesired hyperopic shifts secondary to corneal flattening from the procedure and, despite the use of surface modulators, elimination of pre-existing astigmatism was difficult.

Another potential use of the excimer laser is anterior lamellar keratectomy to smooth an irregular corneal surface. However, if an irregular surface is ablated without masking of the irregularities, the irregular surface contour will simply be reproductive deeper in the cornea.

U.S. Pat. Nos. 4,856,513 to Muller and 4,994,038 to Raven et al., the entire disclosures of which are incorporated by reference, disclose methods and apparatus for the shaping of surfaces using lasers. These patents are in particular directed to methods and apparatus which are described as particularly suited to the treatment of the cornea of an eye, providing a means of effecting reprofiling of the cornea.

U.S. Pat. No. 4,856,513 describes a laser system for reprofiling a surface, comprising a laser and an erodible mask disposed between the laser and the surface for providing a predefined profile of resistance to erosion by laser radiation. The masking means comprises a rigid structure which is affixed to the surface of the eye with a masking lens connected to the support structure and disposed above the cornea. The erodible mask is formed from plastic material, such as poly(methyl methacrylate) or poly(methyl styrene); alternatively, the rigid structure of the masking means may comprise a cup-shaped rim to support a liquid or semi-liquid masking lens. During irradiation, the lens is gradually ablated and an increasing area of the cornea becomes exposed to erosion; the maximum thickness of the lens exceeds the minimum thickness by an amount equal to the maximum depth of the erosion desired.

In addition to the afore-noted type of masking means, U.S. Pat. No. 4,994,038 further discloses an embodiment of masking means in the form of a contact-type lens device which is disposed upon and directly affixed to the surface of the cornea. The contact-type lens is constructed so as to have a first surface contoured to fit to the surface to be eroded and a second surface contoured to provide the desired surface contour following erosion by exposure to laser radiation. The contact-type lens comprises a material which is erodible by laser radiation and preferably has ablation characteristics substantially identical to the object material; once again, plastics material such as poly(methyl methacrylate) and poly(methyl styrene) are proposed.

While providing advantages relative to the direct application of the laser to the corneal surface, an entirely satisfactory method for reshaping the corneal surface has not been provided by using either a rigid structure affixed to the surface of the eye with a masking lens connected thereto (as proposed in U.S. Pat. No. 4,856,513) or a masking means in the form of a contact-type lens made of plastic (as proposed in U.S. Pat. No. 4,994,038). The rigid structure of U.S. Pat. No. 4,856,513 is a cumbersome device and would not be particularly suitable for routine use.

Moreover, both arrangements call for the use of erodible masks which are manufactured based upon measurements of the patient's eye. In principle, the prior art methods call for preformed masks which are configured to take into account both the structure of the surface to be eroded and the desired surface contour following erosion, so as to provide a predefined profile of resistance to erosion by laser irradiation. The preparation of such masks would thus require a complex series of measurements to define the surface to be treated and a manufacturing process which would permit the formation of highly-complex profiles on both surfaces of the mask. With respect to highly scarred or irregular corneas in particular, the preparation of such masks would be extremely difficult if not impossible. The preparation of masks from materials having sufficiently similar ablation characteristics to the surface being treated is also more easily accomplished in theory than in practice.

It is therefore an object of the present invention to provide a method whereby modifications of the cornea by laser treatment may be carried out in a more efficient manner than was heretofore possible with the prior art methods.

In particular, it is an object of the present invention to provide a method for reprofiling the surface of the cornea which does not involve the preparation of complex ablation masks or the use of cumbersome devices for maintaining such ablation masks in a fixed position.

It is a further object of the present invention to provide a method for reprofiling the surface of the cornea which utilizes readily-available materials, including masking materials which have ablation properties substantially identical to those of the cornea.

SUMMARY OF THE INVENTION

In accordance with the present invention, there is provided a method for modification of the corneal surface in which a gel is applied to the cornea and molded in situ to create an ablation mask. This ablation mask has a posterior surface substantially identical to that of the surface to be treated. A lens having a posterior curvature corresponding to the desired final profile of the cornea is superimposed on the gel prior to the setting of the gel; the anterior curvature of the ablation mask is equal to that of the posterior curvature of the lens. By forming an ablation mask in situ upon contact with the surface to which the gel is applied, preparation of a predetermined profiled surface corresponding to a cornea to be treated through the use of elaborate machining is no longer necessary. Moreover, the gel has essentially the identical ablation properties of the cornea, which is generally not the case when other non-biological materials (such as plastics materials) are used. A preferred gel for use in accordance with the present invention is collagen gel.

DETAILED DESCRIPTION OF THE INVENTION

The ability of several fluids of different viscosities to mask deeper tissues while exposing protruding irregularities during PTK procedures has been investigated. A fluid of moderate viscosity was found to adapt closely to the surface being treated, and thus maximally smooth an irregular corneal surface. The optimal material for this purpose was considered to be a biocompatible fluid with three characteristics: the ability to solidify on and adhere to the anterior corneal surface; the capacity to be molded to any desired curvature; and ablation characteristics similar to those of the cornea.

In accordance with the present invention, it has been determined that various transparent biological materials that are ablatable by ultraviolet light meet these characteristics. For example, materials such as collagen, hyaluronic acid, keratin sulfate and high molecular weight glycosaminoglycans have suitable properties for use in accordance with this invention. In particular, various collagen suspensions exhibit all of the characteristics appropriate for use as an ablation mask. For example, a bovine Type I collagen suspension may be maintained in a soluble state at reduced temperatures (e.g., 4° C.); however, at elevated temperatures (e.g., 37° C.) as are achieved upon application of the suspension to the cornea, the collagen solidifies. It has been confirmed that the collagen adheres well to the surface of the cornea and may be molded into a desired shape to form a smooth, firm gel. In addition, the observed ablation characteristics of the collagen gel were substantially the same as those of the cornea; in fact, the experimental difference in mean ablation rates observed was not statistically significant.

In accordance with the present invention, an improved method of reprofiling the surface of a cornea is provided, in which an ablatable masking means comprising a suitable gel is disposed between a laser means and the cornea, and the masking means is irradiated so as to selectively ablate the corneal surface. As is the case with prior art ablation methods, a portion of the radiation from the laser is absorbed by the masking means, while another portion is transmitted to the corneal surface. In this manner, the surface is selectively eroded in accordance with the mask profile. In contrast to the prior art methods, however, the formation of the ablation mask is carried out in situ using a mask material with ablation characteristics essentially identical to those of the surface being treated.

For purposes of the present invention, it is important that the material employed for formation of the masking means have a proven ablation rate comparable to that of corneal tissue. In addition, it is generally appropriate that the material have a water content comparable to that of corneal tissue; this not only prevents water buildup, but also reduces or eliminates any problems which might result from electrostatic attraction of ablated particles for the corneal surface.

A generally preferred material for use in preparation of ablation masks accordance with the present invention is a collagen. There are at least seven types of collagen (generally known as Types I–VII), most of which are expected to be useful in accordance with the present invention. Type I collagen is readily available in large quantities, and is the predominant form of collagen found within the cornea; thus, it is presently a preferred form of collagen for use in accordance with the present invention. Other collagens (for example, human type IV) have been used to manufacture synthetic epikeratophakia lenticules, which are attached to the corneal surface permanently; upon re-epithelialization, the lenticules permanently correct refractive errors [Thompson, K. P. et al., "Current Status of Synthetic Epikeratoplasty," *Refractive & Corneal Surgery* 7:240–248 (1991)]. Therefore, it is contemplated that in addition to the presently preferred type I collagen, other types of collagen as well as noncollagenous compounds having the requisite properties may also be used in accordance with the present invention.

In general, gel-forming materials having the following characteristics are suitable for use in accordance with the present invention: sterility; reasonable shelf life during which the material can be stored prior to use; ability to form a gel within a reasonable period of time; and formation of a transparent or relatively clear gel (rather than an opaque gel), so that the patient can see adequately to maintain fixation on a target during the laser procedure and the surgeon can see the pupil well enough to ensure proper centration.

In addition to suspensions which solidify or gel upon application of heat, it is also contemplated in accordance with the present invention to use formulations in which alternative methods to induce gelling or cross-linking of the gel in situ are employed. For example, formulations which gel upon exposure to ultraviolet light may be useful in accordance with the present invention. In addition, it is also contemplated to use chemically-modified forms of materials such as collagen in which cross-linking is induced upon exposure to oxygen or upon addition of a particular chemical or catalyst.

As described in U.S. Pat. Nos. 4,856,513 and 4,994,058, a suitable laser wavelength is that obtainable from a UV Argon Fluoride laser, typically about 193 nanometers. One exemplary excimer laser for use in accordance with the present invention is available commercially under the designation Twenty-Twenty Excimer Laser from VISX Inc., Sunnyvale, Calif. Irradiation intensities vary depending upon the wavelength of the laser, and there is typically a threshold value of the energy density below which significant ablation does not occur. Irradiation levels above this threshold are essential for ablation. Increases in energy density beyond this point result in corresponding small changes in ablation rate in corneal tissue and the gel. Therefore, it is preferred that the energy density at the surface to be eroded is maintained between the threshold value necessary for ablation and the saturation value. The range of energy densities suitable for use in accordance with the present invention are readily determined on an empirical basis for any given wavelength of laser energy. As indicated in U.S. Pat. No. 4,994,058, for erosion of a mask and the underlying corneal stroma by energy of wavelength 193 nm (as obtained from an argon fluoride excimer laser), the threshold value was found to be about 50 mJ per $cm^2$ per pulse, and the saturation value about 250 mJ per $cm^2$ per pulse; thus, a range of energy densities between about 50 mJ per $cm^2$ per pulse to about 200 mJ per $cm^2$ per pulse, and preferably between about 100 and about 175 mJ per $cm^2$ per pulse, would be suitable for reshaping of corneal tissue. Of course, other ultraviolet wavelengths are also capable of ablating corneal tissue and gel, and suitable ultraviolet wavelengths may be generated by lasers other than the excimer laser.

In addition, as is well known in the art, the pulse repetition rate for the laser may be chosen empirically by routine experimentation for any particular application. As indicated in U.S. Pat. No. 4,994,058, a normal pulse repetition rate may be between 1 and 500 pulses per second. Typically, the laser is set to operate so that a single pulse erodes a depth in the range of about 0.1 to about 1 micrometer of material per pulse.

By using a gel which is not perfectly transparent or colorless, the surgeon is able to visually monitor the progress of the ablation through the gel; the ablation process may then be interrupted when the gel has been ablated as desired. An objective monitoring system may also be employed for this purpose. In general, the excimer laser produces fluorescence when it ablates any biological tissue, including corneal tissue, and particularly the corneal epithelium. This fluorescence is measurable and quantifiable. By appropriate modification of the material used to form the gel, during ablation the gel may be made to fluoresce at a wavelength that is visible and readily identifiable by the surgeon. By quantitatively monitoring emitted fluoresce, the surgeon may thus be able to determine when the gel has been ablated completely.

A significant advantage of the present invention is that use of the novel collagen ablation masks does not require any significant modifications in protocol relative to the heretofore known methods employing excimer lasers for reprofiling of the cornea. For example, as described in U.S. Pat. No. 4,998,058, the laser is generally provided with an optical wave guide to transmit the laser beam output from the laser to the patient; any of a variety of available wave guides, including flexible and rigid guides, may be employed. Similarly, the design of the laser system is not critical to the present invention and a number of commercially-available laser systems familiar to the practitioner may be employed in accordance with the present invention.

In accordance with the present invention, an improved method of reprofiling the surface of a cornea is provided, in which an ablatable masking means comprising a suitable gel is disposed between a laser means and the cornea, and the masking means is irradiated so as to selectively ablate the corneal surface. As is the case with prior art ablation methods, a portion of the radiation from the laser is absorbed by the masking means, while another portion is transmitted to the corneal surface. In this manner, the surface is selectively eroded in accordance with the mask profile. In contrast to the prior art methods, however, the formation of the ablation mask is carried out in situ using a mask material with ablation characteristics essentially identical to those of the surface being treated.

Pursuant to the method of the present invention, an amount of gel sufficient to provide an ablation mask of the desired thickness upon solidification thereof is applied directly to the patient's cornea. The thickness of the ablation mask may be varied within a fairly wide range, depending upon the type of reprofiling contemplated. Suitable maximal thicknesses would be on the order of 10 to 500 micrometers, preferably 100 to 200 micrometers.

A suitable molding device having a posterior curvature corresponding to the desired final profile of the cornea is appropriately centered and superimposed on the gel prior to the setting of the gel. A suitable molding device has a smooth optical finish and transmits heat and ultraviolet light. Such a device may be provided with heating elements and conductive pathways for transfer of heat to the gel so as to obtain a precise, desired temperature over the surface of the gel. Similarly, such a molding device may contain fiberoptic elements arranged so that light from an appropriate visible or ultraviolet light source can be conducted to the surface of the gel, which is then illuminated in a uniform fashion. In one type of embodiment of such a molding device, a handle for the molding portion is provided; the handle may be permanently attached, or it may be constructed such that the molding end may be removed and replaced with other molding ends each having a specified curvature. Fiberoptic bundles or heat-transmitting wires may be supported by the handle, with one end connected to comparable elements in the molding end and the other end operatively connected to a suitable light or heat source, respectively. Such molding devices may be manufactured with curvatures ranging from about 35 to about 50 diopters, suitably in increments of 0.5 diopters. Pursuant to one embodiment of the inventive method, conventional contact lenses having the desired posterior curvature may be employed as molding devices.

Upon solidification of the material used to form ablation mask in situ, the lens or molding device is carefully removed. The resultant ablation mask (having a posterior surface corresponding to the patient's cornea and an anterior surface corresponding to the posterior curvature of the lens or molding device) is then ready for laser ablation. The head of the patient may be provided with some form of restraints to prevent motion during the laser treatment, which follows in a manner known per se for laser ablation treatments without masks or with masks in accordance with the prior art.

Application of a moldable material such as a collagen suspension to mask the anterior corneal surface has been shown to be a useful approach to smoothing corneal irregularities using laser means. Placement of a collagen suspension over artificially created irregularities in the corneal surface demonstrated the ability of this collagen to conform around corneal protrusions, fill depressions and thus create a smooth surface. By masking depressed regions of the cornea, the gel allows protruding corneal irregularities to be exposed first for anterior lamellar keratectomy. In this manner, a portion of the radiation is selectively absorbed by the masking means and another portion is transmitted to the surface, in accordance with the mask profile, to selectively erode the surface. This results in a postoperatively smooth corneal surface.

Prior to corneal ablation, the gel is placed on the cornea and molded with a suitable molding device so as to steepen the anterior surface to be ablated by a desired number of diopters (e.g., 5 or 10). After the gel has set, PTK is performed so as to remove the corneal opacity. By preoperatively steepening the surface, the tendency of the PTK procedure to flatten the cornea is counterbalanced, such that the high hyperopia experienced with PTK would be averted.

The topographic results are also very encouraging in that use of flat and steep contact lenses or other molding devices to mold the gel produced marked flattening and steepening of the anterior surface, respectively, as demonstrated with photokeratoscopy.

The inventive procedure may also be employed for the correction of refractive errors (myopia or hyperopia, with or without astigmatism) with the excimer laser. For example, an individual with five diopters of myopia and a central corneal power of 40 diopters would have the gel molded using a 35 diopter base curvature contact lens or other molding device; a laser would then be used to ablate through the gel, leaving an anterior cornea of 35 diopters.

When using gels which set at elevated temperatures, an incubation time is often required for the gel to solidify under the contact lens or molding device. The collagen suspension alone quickly solidifies at body temperature. When placed under a conventional contact lens, the bovine type I collagen required up to 1 hour and 45 minutes to completely solidify. The discrepancy in time necessary for solidification may be attributed to slow heating of collagen because the plastic of the contact lenses is a poor conductor of heat. The lens may have acted as an insulator, impeding upon the incubator's heat reaching the collagen, and thus necessitating more time to solidify. Following solidification of the collagen, in some instances removal of the contact lens resulted in portions of the collagen gel mold adhering to the lens; this could distort the contour of the mold. The use of a contact lens or other molding device with both a lubricated surface and a heating element would address the above stated limitations.

The data reported herein confirm the capacity of a gel mold to serve as an adjuvant to excimer laser photorefractive keratectomy for smoothing irregular corneal surfaces and for correction of myopia, hyperopia and astigmatism. By using the cornea itself as the template for preparation of the posterior surface of the ablation mask, each unique cornea is readily accommodated. Suitable lenses (such as, for example, conventional hard contact lenses) for virtually any desired final curvature are readily available commercially. The in situ gel ablation mask is used in the same manner as the heretofore known preformed masks (for example, to smooth irregular corneal surfaces) using an excimer laser.

The invention may be better understood with reference to the accompanying examples, which are intended for purposes of illustration only and should not be viewed as in any sense limiting the scope of the invention as described in the claims appended hereto.

EXAMPLE 1

An excimer laser (Twenty-Twenty Excimer Laser, VISX Inc., Sunnyvale Calif.) was used to create the ablation in this study. The laser was adjusted to deliver a fluence of 140 to 160 $mJ/cm^2$ at a frequency of 5 Hz. A hand-held blower that delivers nitrogen gas at a low flow rate was used to remove any material that was released from the cornea surface during the ablations, and a vacuum was used to remove this material as described in clinical studies. The eyes used in this study were pig eyes obtained fresh from a local abattoir. The corneal epithelium was removed with a Paton spatula. The collagen used was a bovine Type 1 collagen, solubilized from defatted tendons by pepsin digestion and purified by three cycles of neutral salt and acid salt precipitations. The final collagen solution (6 mg/ml) was stored at 4° C. in 0.5M acetic acid. Prior to each experiment, aliquots of the solution was dialyzed extensively in 0.05 phosphate buffer containing 0.15M sodium chloride. At 4° C., the collagen is in a soluble state and when placed in an ambient air incubator at 37° C. (body temperature), it solidifies.

To create a collagen mold on a normal corneal surface eleven pig corneas were de-epithelialized as described above. The eye was sutured via the optic nerve in an eye holder to prevent movement of the eye upon vertical placement. A 12 ring keratoscope (Kera Corporation, Santa Clara, Calif.) was used for photokeratoscopy. Following this, the collagen suspension (maintained at 4° C.) was placed via an eye dropper on the posterior surface of a polymethyl methacrylate contact lens (Vision Tech Inc., Phoenix, Ariz.), and another drop was placed on the anterior corneal surface. The contact lens was then placed on the central corneal axis to serve as a mold for the collagen. The eye, with the collagen and the contact lens in place, was moved to an ambient air incubator at 37° C. (body temperature) for 1 hour and 45 minutes. The contact lens was then carefully removed leaving behind a thin, smooth, semi-opaque, firm gel on the anterior corneal surface. Photokeratoscopy was then repeated and the pictures analyzed quantitatively using the kerascan analyzer (Kera Corporation). Split lamp photography was taken to document the appearance of the collagen gel mold and its adherence to the corneal surface. Seven of these corneas were then prepared for scanning electron microscopy and light microscopy. Specimens were fixed in formalin and placed in an incubator (37° C.). The specimens were placed in the incubator during fixation to prevent resolubilizing of the collagen. Those selected for scanning electron microscopy were dehydrated through a graded alcohol series. Alcohol was exchanged for anhydrous carbon dioxide in a critical-point drying apparatus. Mounted samples were sputter coated with gold and palladium to a thickness of 15 microns.

Frozen sections were performed on the corneas after fixation because routine processing and paraffin embedding caused the collagen gel to slip from the surface of the cornea. The sections were stained with hematoxylin and eosin or periodic acid-Schiff.

Four of the eyes with the collagen gel mold, after photokeratoscopy, underwent excimer laser ablations (phototherapeutic keratectomy) followed by slit lamp photography. Specimens were then fixed and processed for light microscopy as described above.

To create a reproducible irregular corneal surface, an excimer laser was used to perform a 150 micron depth ablation on the de-epithelialized cornea after masking the cornea with either a grid or linear screen made of stainless steel. The grid screen resulted in the creation of a grid pattern of square ablated zones, 150 microns deep, with intervening raised ridges; the linear screen created a linear pattern of 150 micron deep ablated zones with intervening raised ridges (shielded by the metal). The ablation treatment zone was 6.0 mm in diameter.

The collagen suspension and a contact lens were then placed on the anterior corneal surface as described above, and the eye placed in an ambient air incubator at 37° C. for 1 hour and 45 minutes. The contact lens was then carefully removed. At this point, the eye was photographed, fixed in formalin and processed for histopathologic examination (as outlined previously), or underwent a second ablation. With the excimer laser, a smoothing procedure was performed on three eyes using an ablation treatment zone of 3 mm within the initial 6 mm treatment zone. This enabled use of the irregular peripheral cornea as an internal control in each photograph to contrast with the central re-ablated region. Split lamp photography, formalin fixation and processing then ensued.

To assess the ablation rate of the collagen gel a 1 cm diameter rubber ring was placed on a plastic plate. The collagen suspension was placed via an eye dropper in the ring, which was then placed in an ambient air incubator at 37° C. for 45 minutes. An optical pachymeter (Carl Zeiss Inc., West Germany) was used to measure collagen thickness. Once this thickness was determined, the excimer laser was programmed to ablate a 4 mm treatment zone at a depth rate of 0.30 micron per pulse. The excimer laser ablated trough the entire thickness of collagen until the plastic plate was reached. The number of pulses required to ablate through the collagen was recorded and the collagen ablation rate determined by dividing the number of pulses by the thickness of the collagen.

To compare ablation rates in cornea and in collagen gel, a similar procedure was performed on pig eyes. The eye was de-epithelialized and sutured in an eye holder as previously described. Optical pachymetry was performed to determine the corneal thickness, following which the excimer laser, with the same settings 4 mm treatment zone and 0.30 micron depth per pulse, was used to ablate through the entire cornea. The number of pulses required to ablate through the cornea was recorded and the cornea ablation rate determined by dividing the number of pulses by the thickness of the cornea.

To examine for corneal refractive differences following placement of the collagen gel mold, a paired T-test was used. The significance level was defined as $P<0.0025$ to adjust for an overall significance level of $P<0.05$. To evaluate differences in ablation rates of collagen and cornea, we used an unpaired T-test with significance level defined as $P<0.05$.

Using a contact lens as a mold, a semi-opaque, firm collagen gel impression was created on the anterior corneal surface. The collagen assumed the contour of the contact lens; slit lamp photography confirmed its adherence to the cornea, as well as its smooth surface. In addition, slit lamp examination showed the thickness of the collagen mold centrally to be approximately one half of the cornea.

Scanning electron microscopy (SEM) of these specimens revealed the close opposition of the collagen to the anterior corneal surface. SEM processing of the specimens requires several dehydration steps and thus the collagen thickness appeared thinner than previously seen with slit lamp examination. The anterior surface of the collagen mold was quite smooth with some irregularities present thought to be SEM processing artifact.

Excimer laser ablations performed through the gel and into the stroma resulted in smooth treatment zones as evident by slit lamp examination and by light microscopy.

Use of the grid and linear metal screens created a checkerboard and linear pattern of corneal surface irregularity, respectively; this resulted in 150 micron deep depressions separated by lines of unablated corneal tissue. Collagen placed on this surface filled the rectangular depressions and thus masked protruding irregularities. Frozen sections of these specimens, despite prior fixation in formalin, showed artifactual displacement of the collagen when viewed by a light microscope. However, in viewing these samples it was evident that the posterior aspect of the collagen complements the irregularities of the anterior corneal surface.

Slit lamp examination of the eyes that had undergone a smoothing procedure with the excimer laser showed elimination of the corneal irregularity within the new treatment zone. Further examination using light microscopy revealed a smooth, flat surface in an area previously occupied by a corneal ridge irregularity.

Using the method, as previously described to create a collagen mold on a normal corneal surface, and using a 35.5 diopter base curvature contact lens, four eye specimens were prepared. Photokeratoscopy of corneas covered with the collagen gel demonstrated round and regular mires. Using the kerascan, quantitative analysis of the keratoscope photographs taken before and after collagen placement was performed. A paired T-test evaluation of the refractive power of each ring, before and after application of collagen, for each individual eye was performed. The analysis involved rings two through six, and the results in all cases showed a flattening of the cornea, as was expected with the flat contact lens used. However, using an alpha level of 0.0025, about half of the reductions in refractive power were statistically significant.

The ablation rates of cornea and collagen were $2897.40 \pm 97.90$ and $2751.40 \pm 422.40$ pulses/mm (mean±standard error), respectively. The difference in mean ablation rates was not statistically significant ($P=0.71$).

EXAMPLE 2

Pig eyes were prepared as in Example 1. The bovine Type 1 collagen was solubilized from defatted skin by pepsin digestion and purified by three cycles of neutral salt and acid salt precipitations. The final collagen solution (10 mg/ml) was stored at 4° C. in 0.5M acetic acid. Prior to each experiment, aliquots of the solution were dialyzed extensively in 0.05 phosphate buffer containing 0.15M salt. At 4° C., the collagen is in a soluble state and when placed in an ambient air incubator at 37° C. (body temperature), it solidifies.

To create a collagen mold on a normal corneal surface the pig eye was deepithelialized in the manner stated above. One to two cc of balanced saline solution was injected in each eye through the optic nerve until the globe was firm. The eye was sutured via the optic nerve in an eye holder so as to prevent movement of the eye upon vertical placement. Keratometer readings (Kera Corporation, Santa Clara, Calif.) were obtained by two independent observers as the eye was frequently washed with physiological balanced salt solution. Subsequently, the eyes were surrounded with tissue paper soaked in balanced saline solution and warmed in an incubator at 37° C. for 30 minutes. During the incubation period, the eyes were moistened every 15 minutes with drops of balanced saline solution. Following this, the collagen suspension (maintained at 4° C.) was placed via an eye dripper on the posterior surfaces of a 35.0 diopter, 45.5 diopter or 52.0 diopter polymethyl methacrylate hard plastic contact lens (Vision Tech Inc., Phoenix, Ariz.), and another drop was placed on the anterior corneal surface. The contact lenses had previously been drilled in the peripherally with six 0.033 mm holes using drill head #66 (V. F. Rogers, Denver, Colo.) to facilitate heat transfer. The contact lens, containing the soluble collagen, was then placed on the central cornea, acting as a mold for the collagen with the 35.5 diopter lens. The eye, with its collagen and contact lens, were placed in an incubator with blower at 37° C. (body temperature) for 1 hour and 15 minute with the two steeper lenses, eyes were incubated at 47° for 45 minutes, because preliminary experiments showed this higher temperature was necessary to cause gelation of the collagen. The contact lens was then carefully removed, leaving behind a thin, smooth, semi-opaque, firm gel on the anterior corneal surface. Keratometer readings were then obtained by the same two independent observers as the eye was frequently washed with a physiological Ph balanced salt solution.

Mean keratometric reading for the two principal meridian of each eye for each observer was determined. Keratometric astigmatism was determined by the difference between the two principal meridian for each eye, for each observer. Subsequently, the mean pre-collagen keratometric astigmatism for each eye was calculated and the total population of eyes were separated into two groups. Group #1, consisted of six eyes, having keratometric astigmatism greater than or equal to 1.00 diopter and Group #2, consisted of six eyes, each with a keratometric astigmatism less than 1.00 diopters.

Analysis of variance with repeated measure design was performed to evaluate differences between pre- and post-collagen keratometric readings an keratometric astigmatism. The model incorporated the design of two observers pre-and post-collagen keratometric readings for each eye. Results are reported as Man$\rightleftharpoons$SEM. A P value of less than 0.05 was considered significant.

Using a contact lens as a mold, the collagen suspension polymerized into a semi-opaque, firm gel on the anterior corneal surface. The collagen assumed the contour of the contact lens and slit lamp examination revealed its smooth surface as well as its adherence to the anterior corneal surface.

The mean pre-collagen keratometric reading for the four eyes in the 35.0 diopter contact lens group ranged from 38.75 to 40.80 diopter with a group mean of 39.67±0.41 diopters (Mean±SE). The mean post-collagen keratometric reading for the same group ranged from 34.25 to 36.15 diopters with a group mean of 34.91±0.37 and this value was significantly different as compared to the group mean pre-collagen mean keratometric reading, P=0.0001 (Table 1). The post-collagen mean keratometric value was not significantly different from the base curvature of the 35.0 diopter contact lens used, P=0.74.

The mean pre-collagen keratometric reading for the four eyes in the 45.5 diopter contact lens group ranged from 38.12 to 39.38 diopter with a group mean of 38.93±0.22 diopters (Mean±SE). The mean post collagen keratometric reading for the same group ranged from 44.13 to 45.68 diopters with a group mean of 44.83±0.30 and this value was significantly different as compared to the group mean pre-collagen keratometric reading, P=0.0001 (Table 1). The post-collagen mean keratometric value was determined significantly flatter than the base curvature of the 45.5 diopter contact lens used, P=0.02.

The mean pre-collagen keratometric reading for the four eyes in the 52.0 diopter contact lens group ranged from 38.25 to 41.75 diopter with a group mean of 39.81±0.67 diopters (Mean±SE). The mean post-collagen keratometric reading for the same group ranged from 49.25 to 52.50 diopters with a group mean of 50.56±0.55 and this value was significantly different as compared to the group mean pre-collagen keratometric reading, P=0.0001 (Table 1), and significantly different from the base curvature of the 52.0 diopter contact lens used (P=0.01).

In group #1 pre-collagen keratometric astigmatism ranged from 1.5 to 5.25 diopters with a group mean of 2.48±0.43 diopters. Post-collagen keratometric astigmatism ranged from 0.3 to 1.5 with a group mean of 0.504±0/09 and this value was significantly different from the group mean pre-collagen astigmatism, P=0.0001 (Table 2). In group #2 pre-collagen keratometric astigmatism ranged from 0.00 to 1.35 diopters with a group mean of 0.45±0.10 diopters. Post-collagen keratometric astigmatism ranged from 0.1 to 1.5 with a group mean of 0.58±0.15 and this value was not significantly different from the group mean pre-collagen astigmatism, P=0.58 (Table 2). The post collagen keratometric astigmatism for all eyes, regardless of the pre-collagen keratometric astigmatism, was 0.54±0.08 diopters.

Topographic results confirm the capacity of the collagen suspension to form a gel and reproducibly alter the anterior corneal curvature in accordance with the base curvature of contact lens used as the mold. With the 35.0 diopter contact lens, the mean post-collagen anterior corneal curvature was not significantly different from the base curve of the contact lens. However, for eyes in the 45.5 and 52.0 diopters contact lens group, the mean post collagen anterior corneal curvature was about 0.7 and 1.5 diopters less than intended, respectively, significantly different from the base curvature of the contact lenses used. The above observation may be due to the necessity of incubating the collagen incubated at a critical temperature for a critical period of time. The gel can be either incompletely polymerized or over-polymerized and dehydrated, leading to partial adherence to the contact lens or contraction of the gel leading to a significant discrepancy between the post-collagen anterior corneal curvature and the base curvature of the contact lens used.

In preliminary trial using steeper lenses (45.5 and 52.0 diopters) in 37.0 C incubators, complete polymerization of the collagen gel was not observed. Steeper lenses require a greater volume of collagen, hence are not dependent on heat transfer across the contract lens for complete polymerization of collagen gel. Thus, incubation at 47° C. with blower for improved convection and distribution of heat was performed. In view of the possibility of corneal thermal injury at 47° C., other modalities for polymerization of the collagen to address the above limitations are being investigated.

Analysis of keratometric astigmatism clearly demonstrates that significant reduction in eyes with pre-existing astigmatism can be achieved, while no significant astigmatism was induced in eyes where pre-existing astigmatism was not observed.

What is claimed is:

1. A method of reprofiling a corneal surface using a laser means operable to deliver laser radiation to the surface, comprising:
   disposing an ablatable masking means between the laser means and the corneal surface, the masking means comprising a gellable liquid or semi-solid composition applied onto the corneal surface;
   applying a shaping means to said masking means thereby forming a shaped masking means;
   removing said shaping means;
   allowing said shaped masking means to gel on the corneal surface; and
   irradiating the shaped masking means and corneal surface so as to selectively ablate the shaped masking means and the corneal surface, the corneal surface being selectively ablated in accordance with the shape of the shaped masking means.

2. A method according to claim 1, wherein said shaped masking means has a posterior surface curvature substantially identical to that of the corneal surface.

3. A method according to claim 2, wherein said shaping means has a predetermined posterior curvature thereby forming, when said shaping means is applied to said masking means, a shaped masking means having an anterior surface curvature substantially identical to the posterior curvature of the shaping means.

4. A method according to claim 3, wherein said shaping means is a contact lens.

5. A method according to claim 3, wherein said shaping means comprises means for transmitting light to said gellable liquid or semi-solid composition for facilitating gelling thereof.

6. A method according the claim 3, wherein said shaping means comprises means for transmitting heat to said gellable liquid or semi-solid composition for facilitating gelling thereof.

7. A method according to claim 1, wherein said gellable liquid or semi-solid composition is selected from the group consisting of collagen, hyaluronic acid, keratin sulfate and high molecular weight glycosaminoglycans.

8. A method according to claim 1, further comprising monitoring ablation through the masking means.

9. A method according to claim 8, wherein said monitoring is carried out by visual observation.

10. A method according to claim 8, wherein said monitoring is carried out by measurement of fluorescence produced by the laser means when it ablates the corneal surface.

* * * * *